US00PP17429P2

(12) United States Plant Patent
Post

(10) Patent No.: US PP17,429 P2
(45) Date of Patent: Feb. 20, 2007

(54) ***CHRYSANTHEMUM* PLANT NAMED 'LEON'**

(50) Latin Name: *Chrysanthemum×morifolium*
Varietal Denomination: Leon

(75) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 11/188,968

(22) Filed: Jul. 25, 2005

(51) Int. Cl.
*A01H 5/00* (2006.01)

(52) U.S. Cl. ..... Plt./297

(58) Field of Classification Search ..... Plt./297
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Leon', characterized by its daisy-type inflorescences with pink-colored ray florets; freely flowering habit; early and uniform flowering response; and good postproduction longevity.

1 Drawing Sheet

Botanical designation: *Chrysanthemum×morifolium.*
Cultivar denomination: 'Leon'.

BACKGROUND OF THE INVENTION

The present invention relates to a new and distinct cultivar of *Chrysanthemum* plant, botanically known as *Chrysanthemum×morifolium* and referred to by the name 'Leon'.

The new *Chrysanthemum* is the product of a planned breeding program conducted by the Inventor in 's Gravenzande, The Netherlands. The objective of the breeding program is to create new vigorous cut *Chrysanthemum* cultivars with interesting inflorescence forms and attractive floret coloration.

The new *Chrysanthemum* originated from a cross-pollination on Mar. 14, 2001 in 's Gravenzande, The Netherlands, of the *Chrysanthemum×morifolium* cultivar Grand Pink, not patented, as the female, or seed, parent with a proprietary seedling selection of *Chrysanthemum×morifolium* identified as code number 20199, not patented, as the male, or pollen, parent. The new *Chrysanthemum* was discovered and selected by the Inventor as a single plant within the progeny of the stated cross-pollination in a controlled environment in 's Gravenzande, The Netherlands.

Asexual reproduction of the new *Chrysanthemum* by terminal cuttings in a controlled environment in 's Gravenzande, The Netherlands since Jun. 22, 2002, has shown that the unique features of this new *Chrysanthemum* are stable and reproduced true to type in successive generations.

BRIEF SUMMARY OF THE INVENTION

The cultivar Leon has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Leon'.

These characteristics in combination distinguish 'Leon' as a new and distinct cultivar:

1. Daisy-type inflorescences with pink-colored ray florets; typically grown as a spray-type.
2. Vigorous growth habit.
3. Freely flowering habit.
4. Early and uniform flowering response.
5. Good postproduction longevity.
6. Resistant to White Rust.

Plants of the new *Chrysanthemum* can be compared to plants of the female parent, the cultivar Grand Pink. In side-by-side comparisons conducted in 's Gravenzande, The Netherlands, plants of the new *Chrysanthemum* differed from plants of the cultivar Grand Pink in the following characteristics:

1. Plants of the new *Chrysanthemum* were more tolerant to high temperatures than plants of the cultivar Grand Pink.
2. Plants of the new *Chrysanthemum* had more durable leaves that were less sensitive to climatic stresses than plants of the cultivar Grand Pink.

Plants of the new *Chrysanthemum* can be compared to plants of the male parent selection. In side-by-side comparisons conducted in 's Gravenzande, The Netherlands, plants of the new *Chrysanthemum* differed from plants of the male parent selection in the following characteristics:

1. Plants of the new *Chrysanthemum* were more vigorous than plants of the male parent selection.
2. Plants of the new *Chrysanthemum* had spatulate to oblong-shaped ray florets whereas plants of the male parent selection had quill-shaped ray florets.
3. Plants of the new *Chrysanthemum* and the male parent selection differed in ray floret coloration as plants of the male parent selection had soft pink-colored ray florets.

Plants of the new *Chrysanthemum* can be compared to plants of the *Chrysanthemum* cultivar Asenka, not patented. In side-by-side comparisons conducted in 's Gravenzande, The Netherlands, plants of the new *Chrysanthemum* differed primarily from plants of the cultivar Asenka in the following characteristics:

1. Plants of the new *Chrysanthemum* and the cultivar Asenka differed in spray formation as plants of the cultivar Asenka had a more dome-shaped spray formation.
2. Plants of the new *Chrysanthemum* and the cultivar Asenka differed in ray floret coloration as plants of the cultivar Asenka had darker pink-colored ray florets.

Plants of the new *Chrysanthemum* can also be compared to plants of the *Chrysanthemum* cultivar Dekfullham, disclosed in U.S. Plant Pat. No. 16,364. In side-by-side comparisons conducted in 's Gravenzande, The Netherlands, plants of the new *Chrysanthemum* differed primarily from plants of the cultivar Dekfullham in the following characteristics:

1. Plants of the new *Chrysanthemum* had slower developing disc florets that were green in color whereas plants of the cultivar Dekfullham had faster developing disc florets that were yellow green in color.
2. Plants of the new *Chrysanthemum* and the cultivar Dekfullham differed in ray floret coloration as plants of the cultivar Dekfullham had darker pink-colored ray florets.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Leon'.

The photograph at the bottom of the sheet are close-up views of the upper and lower surfaces of typical inflorescences and leaves of 'Leon'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the spring and early summer in 's Gravenzande, The Netherlands, under commercial practice in a glass-covered greenhouse. Plants were initially given long day/short night treatments followed by short day/long night treatments to induce flower initiation and development. During the production of the plants, day temperatures averaged 18° C., night temperatures averaged 17° C. and light levels were about 4,000 lux. Plants were grown as spray-types and were about ten weeks from planting when the photographs and the description were taken.

Botanical classification: *Chrysanthemum×morifolium* cultivar Leon.

Commercial classification: Daisy-type *Chrysanthemum* typically grown as a spray-type cut flower.

Parentage:

*Female, or seed, parent.*—*Chrysanthemum×morifolium* cultivar Grand Pink, not patented.

*Male, or pollen, parent.*—Proprietary seedling selection of *Chrysanthemum×morifolium* identified as code number 20199, not patented.

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 12 days at 20° C.

*Time to produce a rooted cutting, winter.*—About 14 days at 18° C.

*Root description.*—Fine and freely branching; white in color.

Plant description:

*Appearance.*—Herbaceous daisy-type cut *Chrysanthemum;* typically grown as a spray-type; erect and strong flowering stems.

*Growth rate.*—Rapid; vigorous.

*Flowering stem description.*—Length: About 90 cm. Diameter: About 6 mm. Strength: Strong. Aspect: Erect. Color: 146B.

*Foliage description.*—Arrangement: Alternate. Length: About 7.5 to 12.5 cm. Width: About 5 to 8.5 cm. Apex: Cuspidate. Base: Attenuate. Margin: Pinnately lobed; serrate. Texture, upper and lower surface: Pubescent. Petiole length: About 3 to 3.5 cm. Color: Developing foliage, upper surface: Darker than 147A. Developing foliage, lower surface: 137B. Fully expanded foliage, upper surface: Close to 137B. Fully expanded foliage, lower surface: Close to 147B. Venation, upper surface: 146B. Venation, lower surface: 146C. Petiole, upper and lower surfaces: 146C.

Inflorescence description:

*Appearance.*—Daisy-type inflorescence form with spatulate to oblong-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 50 days later. Early and uniform flowering response.

*Postproduction longevity.*—Cut inflorescences will maintain good substance and form for about 3.5 weeks.

*Quantity of inflorescences per flowering stem.*—About 18 inflorescences per flowering stem.

*Inflorescence size.*—Diameter: About 7 cm. Depth (height): About 2.5 cm. Diameter of disc: About 1.5 cm.

*Inflorescence buds.*—Length: About 1 cm. Diameter: About 1.2 cm. Shape: Globular. Color: 137C.

*Ray florets.*—Length: About 3 to 3.5 cm. Width: About 1.4 cm. Shape: Spatulate to oblong. Apex: Emarginate. Base: Acuminate. Margin: Entire. Texture, upper and lower surfaces: Smooth, glabrous; satiny. Number of ray florets per inflorescence: About 21 in about two whorls. Color: When opening, upper surface: 84B. When opening, lower surface: 84C. Fully opened, upper surface: N78C to N78D. Fully opened, lower surface: 76C.

*Disc florets.*—Shape: Tubular. Length: About 5 mm. Width: About 1 mm. Number of disc florets per inflorescence: About 240. Color: Immature: Towards the base, 145D; towards the apex, 145A. Mature: N144B.

*Peduncles.*—Length, terminal peduncle: About 1 cm. Length, fourth peduncle: About 5 cm. Diameter: About 3 mm. Strength: Moderately strong. Texture: Pubescent. Color: 146A to 146B.

*Reproductive organs.*—Androecium: Present on disc florets only. Anther color: Close to 9A. Pollen color: Close to 9A. Gynoecium: Present on both ray and disc florets.

*Seed/fruit.*—Seed and fruit production has not been observed.

Disease/pest resistance: Plants of the new *Chrysanthemum* have been observed to be resistant to White Rust. Resistance to known *Chrysanthemum* pests and other pathogens has not been observed on plants of the new *Chrysanthemum.*

Temperature tolerance: Plants of the new *Chrysanthemum* have been observed to tolerate temperatures from 14° C. to 35° C.

It is claimed:

1. A new and distinct cultivar of *Chrysanthemum* plant named 'Leon', as illustrated and described.

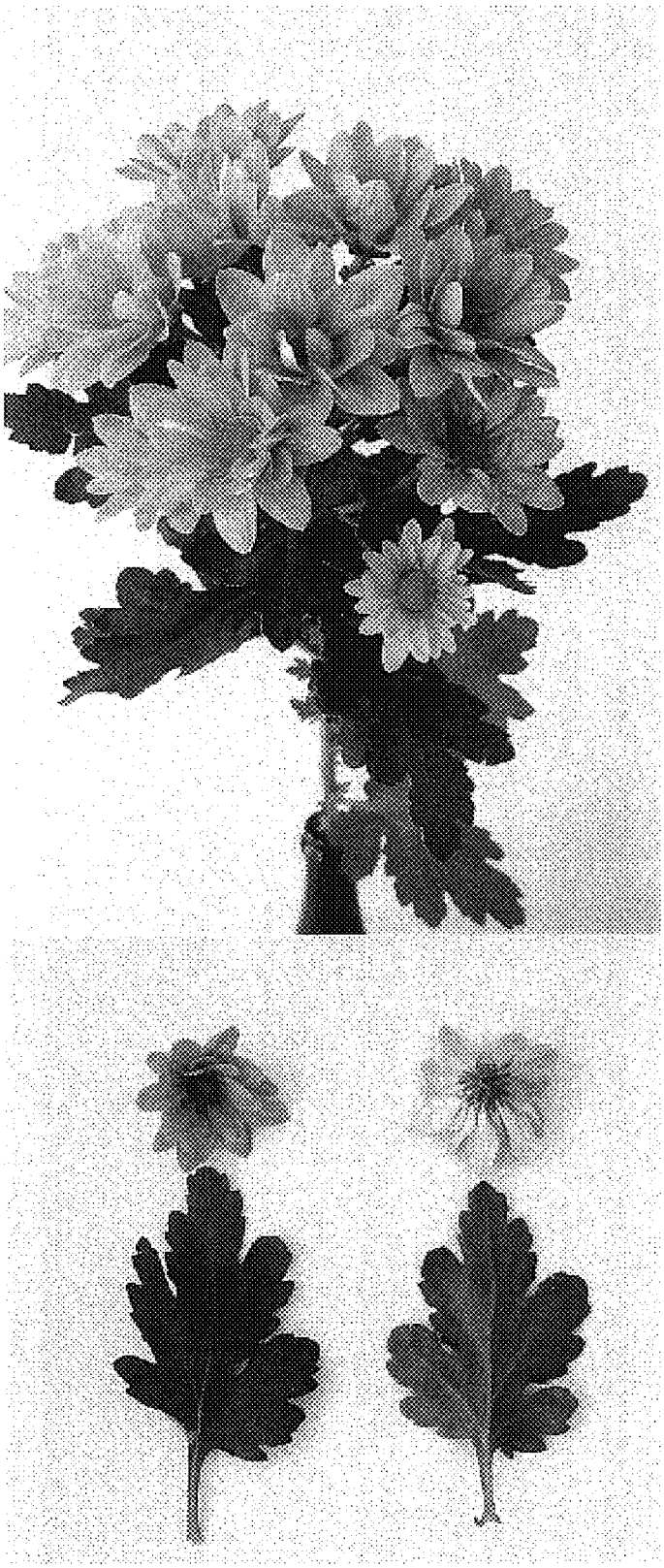

* * * * *